(12) United States Patent
Chabrillangeas et al.

(10) Patent No.: US 12,403,075 B2
(45) Date of Patent: Sep. 2, 2025

(54) COSMETIC COMPOSITION IMPARTING A NATURAL COMPLEXION AND A HEALTHY-LOOKING APPEARANCE EFFECT

(71) Applicant: L'OREAL, Paris (FR)

(72) Inventors: Mathieu Chabrillangeas, Chevilly La Rue (FR); Sonia Eyraud, Chevilly La Rue (FR)

(73) Assignee: L'OREAL, Paris (FR)

( * ) Notice: Subject to any disclaimer, the term of this patent is extended or adjusted under 35 U.S.C. 154(b) by 337 days.

(21) Appl. No.: 15/770,847

(22) PCT Filed: Oct. 25, 2016

(86) PCT No.: PCT/EP2016/075704
§ 371 (c)(1),
(2) Date: Apr. 25, 2018

(87) PCT Pub. No.: WO2017/072129
PCT Pub. Date: May 4, 2017

(65) Prior Publication Data
US 2018/0318186 A1 Nov. 8, 2018

(30) Foreign Application Priority Data
Oct. 26, 2015 (FR) ...................... 1560214

(51) Int. Cl.
| | | |
|---|---|---|
| *A61K 8/26* | (2006.01) | |
| *A61K 8/02* | (2006.01) | |
| *A61K 8/19* | (2006.01) | |
| *A61K 8/20* | (2006.01) | |
| *A61K 8/25* | (2006.01) | |
| *A61K 8/29* | (2006.01) | |
| *A61Q 1/02* | (2006.01) | |

(52) U.S. Cl.
CPC .............. *A61K 8/26* (2013.01); *A61K 8/0241* (2013.01); *A61K 8/19* (2013.01); *A61K 8/20* (2013.01); *A61K 8/25* (2013.01); *A61K 8/29* (2013.01); *A61Q 1/02* (2013.01); *A61K 2800/412* (2013.01); *A61K 2800/43* (2013.01); *A61K 2800/621* (2013.01); *A61K 2800/651* (2013.01)

(58) Field of Classification Search
CPC .......... A61K 8/26; A61K 8/0241; A61K 8/19; A61K 8/20; A61K 8/25; A61K 8/29; A61K 2800/412; A61K 2800/43; A61K 2800/621; A61K 2800/651; A61K 8/06; A61K 8/21; A61Q 1/02; A61Q 1/00; A61Q 19/00
See application file for complete search history.

(56) References Cited

U.S. PATENT DOCUMENTS

2004/0018161 A1* 1/2004 Shah .................. A61Q 1/02
424/63

FOREIGN PATENT DOCUMENTS

| EP | 1433460 A1 | 6/2004 |
|---|---|---|
| FR | 2829022 A1 | 3/2003 |
| WO | 2013170478 A1 | 11/2013 |
| WO | WO 2013/170478 * | 11/2013 |
| WO | 2014012230 A1 | 1/2014 |
| WO | 2016091930 A1 | 6/2016 |

OTHER PUBLICATIONS

Anonymous. Aston Chemicals [online]| 2015; downloaded from <URL http://www.aston-chemicals.com/single-product?id=84> on Feb. 29, 2020; 1 page. (Year: 2015).*

* cited by examiner

*Primary Examiner* — David Browe
(74) *Attorney, Agent, or Firm* — McNees Wallace & Nurick LLC

(57) ABSTRACT

The present invention relates to a cosmetic composition comprising, in a physiologically acceptable medium, composite particles comprising a substrate formed from mica and from bismuth oxychloride coated with at least one mineral pigment and at least one nacre, chosen from composite particles comprising at least one support chosen from mica, synthetic fluorphlogopite or calcium sodium borosilicate, and completely or partially coated with one or more layers of metal oxides, in particular chosen from titanium dioxide, iron oxide, tin oxide and mixtures thereof.
It also relates to the process for giving skin, and in particular facial skin, a uniform complexion and a rosy tonality, while at the same time retaining the natural appearance of the skin, which consists in applying at least one coat of a composition as defined above to the surface of the targeted skin.

21 Claims, No Drawings

COSMETIC COMPOSITION IMPARTING A NATURAL COMPLEXION AND A HEALTHY-LOOKING APPEARANCE EFFECT

The subject of the present invention is a cosmetic composition intended for application to the skin, in particular intended for skin care, capable of giving the skin a healthy-looking appearance, while at the same time retaining its natural appearance.

A composition according to the invention is in particular intended to be applied to the skin, in particular facial skin.

It is common for individuals to seek to make their complexion more luminous and more uniform, while at the same time retaining a non-shiny appearance.

It is known that the skin can lose its brightness, its radiance or become lifeless over time, and the effect of ageing, because of environmental factors such as pollution, wind or cold, for psychological reasons such as fatigue or stress or else because of hormonal changes such as the menopause. Likewise, some skins can exhibit a dull complexion with a grayish coloring.

It is also observed that some mature skins, or even skins of the over fifties, can exhibit a yellowish or greenish complexion.

Consequently, there remains a need for a cosmetic composition which makes it possible to return to a complexion, that offers a more radiant, more uniform appearance, in summary to provide a healthy-looking appearance.

Conventionally, in order to obtain this healthy-looking appearance, use is made of makeup products containing colorants or pigments at individual concentrations generally greater than 1% by weight of the composition (foundations, "BB cream" compositions) which have the distinctive characteristic:
- of generating a strong covering effect,
- of providing an effect that is not very natural/unnatural, in particular due to a lack of match between the skin finish of the composition applied and the skin complexion of the consumer, and
- of causing a negative impact on the cosmetic properties of the base of the composition, namely the composition considered without said colorants or pigments, precisely because of this content of colorants or pigments.

Thus, in relation to the covering effect, the use of compositions comprising a content of colorants or pigments may be curbed in the sense that the following unwanted effects are observed: lack of uniformity at the time of application and problem of traces and of non-uniformity after application.

Likewise, in relation to the cosmetic properties, the following unwanted effects have been listed by users of foundations or of "BB cream" compositions: dragging effect on application, lesser perception of hydration, drying out effect on the skin, feeling of a dry, or even coarse, skin.

In other words, as indicated above, the use of conventional compositions intended to improve the healthy-looking appearance in reality provides an imperfect, not very uniform colored effect, sometimes a metallized appearance which is not very natural, which has the major drawback of masking the natural appearance of the skin. After application, these compositions do not therefore give the skin a natural effect.

There is therefore a need to have available cosmetic compositions which make it possible to confer on the skin a better brightness, and also a healthy-looking appearance, while at the same time retaining its natural appearance and advantageous cosmetic properties, in particular in terms of sensoriality.

Contrary to all expectation, the inventors have discovered a means for giving cosmetic compositions an ability to satisfy all of these objectives.

Thus, according to one of its first aspects, a subject of the invention is a cosmetic composition comprising, in a physiologically acceptable medium, composite particles comprising a substrate formed from mica and from bismuth oxychloride coated with at least one mineral pigment and at least one nacre, chosen from composite particles comprising at least one support chosen from mica, synthetic fluorphlogopite or calcium sodium borosilicate, and completely or partially coated with one or more layers of metal oxides, in particular chosen from titanium dioxide, iron oxide, tin oxide and mixtures thereof.

Such a composition is in particular intended to give the skin to which it is applied a uniform, healthy-looking complexion and to provide a rosy tonality, while at the same time retaining the natural appearance of the skin. Such a composition can also, where appropriate, have a skin imperfection concealing effect. Cosmetic properties similar to those pertaining to compositions intended for skin care are obtained. In particular, the use of such a composition makes it possible to provide cosmetic properties, and more particularly improved sensory properties, for the consumer, concerning the glidance during application and also the softness and comfort after use.

Unexpectedly, the inventors have thus observed that the particular combination of at least one nacre with a composite particle comprising a substrate formed from mica and from bismuth oxychloride coated with at least one mineral pigment makes it possible, in the absence of any additional colorant, to give the skin back a brightness, to give a healthy-looking appearance, in particular to lifeless, dull, ashen or grayish skin, or else to skin which exhibits a yellowish or greenish complexion.

The inventors have also observed that this combination makes it possible, where appropriate, to improve the appearance of the skin, in particular by attenuating the skin imperfections, the marks and the lesions.

Furthermore, despite their properties indicated above, the compositions according to the invention allow the skin to retain a natural appearance, due in particular to the absence of additional colorants.

Moreover, the composition according to the present invention has the advantage of guaranteeing simultaneously a beneficial effect on the complexion, reflected by an immediate healthy-looking/luminous effect and the maintaining of the cosmetic properties, and more particularly sensory properties concerning the glidance on application, and feelings of softness and comfort for the user after application.

The present invention also has the advantage that all of these properties are obtained immediately after applying the composition to the skin.

According to one particular embodiment of the invention, the composition is intended for application to mature skin, or even to skin described as of the over fifties.

A composition according to the invention is thus particularly suitable for being applied to mature skin or skin of the over fifties exhibiting a dull, lifeless complexion which is not very luminous or not at all luminous and which can reveal marks and/or non-uniformities.

A subject of the present invention is thus also a process for giving skin, and in particular facial skin, a uniform healthy-looking complexion and a rosy tonality, while at the same time retaining the natural appearance of the skin, which consists in applying at least one coat of a composition in accordance with the invention to the targeted skin surface, in particular facial skin.

For the purposes of the present invention, the term "color system" denotes the particular combination of at least one nacre with a composite particle comprising a substrate formed from mica and from bismuth oxychloride coated with at least one mineral pigment, in particular of red, pink or red-pink tonality or color.

Moreover, in the context of the present invention, the terms "cosmetic property" and "cosmeticity" can be used without implied distinction.

The term "healthy-looking appearance" means the obtaining of a rosy and bright complexion.

The complexion can be defined in the context of the present invention by the phototypes defined in the classification by Fitzpatrick (see in particular Fitzpatrick, T. B., 1975, "Soleil et peau" ["Sun and skin"], Journal de Médecine Esthétique (2): 33-34; Pathak, M. A.; Jimbow, K.; Szabo, G.; Fitzpatrick, T. B. (1976). "Sunlight and melanin pigmentation". In Smith, K. C. (ed.): Photochemical and photobiological reviews, Plenum Press, New York, 1976: 211-239; Fitzpatrick, T. B. (1986). "Ultraviolet-induced pigmentary changes: Benefits and hazards", Therapeutic Photomedicine, Karger, vol. 15 of "Current Problems in Dermatology", 1986: 25-38).

The compositions according to the invention are particularly suitable for phototypes I to V, and more preferentially to phototypes I to III.

Composite Particle Comprising a Substrate Formed from Mica and from Bismuth Oxychloride Coated with at Least One Pigment The composition according to the present invention comprises composite particles comprising a substrate formed from mica and from bismuth oxychloride coated with at least one mineral pigment.

The substrate formed from mica and from bismuth oxychloride may be in any form. It may in particular be in the form of flakes or flocks.

According to one particular embodiment, the mineral pigment gives the composition a warm tonality or color, and even more particularly a pink, and preferably red-pink, color.

The mineral pigment in itself can have a pink, red or red-pink color.

For the purposes of the present invention, the term "pigments" is intended to mean colored mineral particles which are insoluble in an aqueous medium and which are intended to color the composition and/or the resulting deposit. In the context of the invention, said pigments are not intended to opacify the composition and/or the deposit resulting therefrom.

The term "mineral pigment" is intended to mean any pigment that satisfies the definition in Ullmann's encyclopedia in the chapter on inorganic pigments.

Preferentially, the mineral pigments used in the present invention are iron oxides, preferably giving the composition a warm tonality or color, and even more particularly a pink, and preferably red-pink, color. In other words, in this embodiment, it is a question of preferring red iron oxides.

The color of the composition or of the pigments in themselves can advantageously be evaluated by colorimetric measurements of the lightness (L*) and of the saturation (c*) in the CIE Lab 1976 colorimetric space, and can for example be carried out using a Minolta colorimetric Chromameter CR400®.

The substrate formed from mica and from bismuth oxychloride can be prepared according to techniques well known to those skilled in the art.

According to one particular embodiment of the invention, the particles have an average size, in particular measured by light diffraction, of between 2 and 70 µm, for example between 5 and 60 µm, and more preferentially between 10 and 40 µm.

According to one particular embodiment of the invention, the composite particles are chosen from a substrate formed from mica and from bismuth oxychloride coated with iron oxide, in particular red iron oxide.

According to one particular mode of the invention, the composition comprises composite particles in which a substrate formed from mica and from bismuth oxychloride is coated with iron oxide, in particular red iron oxide, such as those sold under the brand Chroma-Lite Red CL 4506 ® by the company BASF Personal Care Ingredients or else as sold in the Bismica range by the company Farmaquimia.

The composite particles in accordance with the present invention are present in a composition according to the present invention in a content ranging from 0.15% to 0.75% by weight, relative to the total weight of the composition, in particular in a content ranging from 0.2% to 0.5% by weight.

Nacres

In addition to the composite particles comprising a substrate formed from mica and from bismuth oxychloride coated with at least one mineral pigment, as indicated above, a cosmetic composition in accordance with the invention also comprises at least one nacre chosen from composite particles comprising at least one support chosen from mica, synthetic fluorphlogopite or calcium sodium borosilicate, and completely or partially coated with one or more layers of metal oxides, in particular chosen from titanium dioxide, iron oxide, tin oxide and mixtures thereof. In one preferred embodiment, said nacre is chosen from composite particles comprising at least one support chosen from mica, synthetic fluorphlogopite, calcium sodium borosilicate and completely or partially coated with at least one layer of titanium dioxide.

The term "nacre" denotes particles in the form of a plurality of fine platelets with a high refractive index, which each partially reflect and transmit the incident light, these particles also being known as "interference pigments".

According to one particular embodiment of the invention, the color system according to the present invention is formed from composite particles comprising a substrate formed from mica and from bismuth oxychloride coated with at least one mineral pigment and with a single nacre. According to this same embodiment, the cosmetic composition according to the present invention preferably comprises just one nacre.

According to one particular embodiment, the support is synthetic fluorphlogopite.

According to another particular embodiment, the support preferably represents 28% to 90% by weight, relative to the total weight of the particle.

According to yet another embodiment, the titanium dioxide is present in the nacres in a content ranging from 1% to 55% by weight, relative to the total weight of the particle.

According to one particular embodiment, the nacres also comprise iron oxide, in particular in a content ranging from 0.5% to 60% by weight, preferably from 0.5% to 45% by weight, preferentially from 0.5% to 25% by weight, relative to the total weight of the nacres.

By way of iron oxide, mention may be particularly made of brown iron oxide, yellow iron oxide, black iron oxide, brown-ferric blue iron oxide or else a mixture thereof.

According to yet another embodiment, the nacres also comprise tin oxide, in particular in a content of less than 15% by weight, preferably less than 5% by weight, preferably less than 2% by weight, relative to the total weight of the nacres.

The iron oxide and the tin oxide can be present in different layers of the titanium dioxide layer or as a mixture with the layer constituting it.

In one preferred embodiment, the nacre particles have a volume average diameter (De Brouckere diameter) D[4,3] ranging from 10 to 40 μm, preferably from 15 to 35 μm.

Most particularly suitable for the invention are nacres based on a synthetic fluorphlogopite support coated with at least one titanium dioxide layer, and optionally comprising one or more layers of tin oxide and/or of iron oxide, preferentially one or more layers of tin oxide and of iron oxide.

In one preferred mode, the nacre is composed of 73% of synthetic fluorphlogopite, 24% of titanium dioxide (preferably CI77891), 2% of iron oxide (preferably red, CI77491) and 1% of tin oxide.

According to one particular mode of the invention, the composition comprises fluorphlogopite particles coated with a mixture of titanium dioxide, tin oxide and iron oxide, as sold under the brand Syncrystal Ivory by the company Eckart.

According to one particular embodiment, the nacres can also comprise cochineal carmine, chromium oxide.

The nacre is present in a composition of the invention in a content ranging from 0.25% to 0.75% by weight, preferably between 0.3% and 0.6% by weight, relative to the total weight of the composition.

According to one embodiment, a composition in accordance with the invention comprises, by way of color system, a mixture of composite particles comprising a substrate formed from mica and from bismuth oxychloride coated with at least one mineral pigment, in particular a mineral pigment of red, pink or red-pink tonality or color, and at least one nacre as defined above, in particular at least one nacre based on a fluorphlogopite support coated with titanium dioxide, with tin oxide and with iron oxide.

According to an even more particular embodiment, a composition in accordance with the invention comprises, by way of color system, a mixture of composite particles comprising a substrate formed from mica and from bismuth oxychloride coated with at least one red iron oxide and with a single nacre as defined above, and more particularly a nacre based on a fluorphlogopite support coated with titanium dioxide, with tin oxide and with iron oxide.

In all of these embodiments, the ingredients of the color system can be present in a weight ratio of composite particles comprising a substrate formed from mica and from bismuth oxychloride coated with at least one mineral pigment/nacres ranging from 1/5 to 3/1.

Composition According to the Invention

Since the composition according to the invention is intended for topical application to the skin or skin appendages, it contains a physiologically acceptable medium. The term "physiologically acceptable medium" is intended to mean a medium compatible with the skin, the lips, the scalp and/or the hair.

The composition according to the invention may be in any of the galenical forms conventionally used for topical applications and in particular in the form of a dispersion of aqueous gel or lotion type, of an emulsion with a liquid to semi-solid consistency, obtained by dispersion of a fatty phase in an aqueous phase (O/W) or conversely (W/O), or of a liquid to semi-solid suspension of emulsified gel or cream type. According to one preferred mode, the composition is in the form of a direct (O/W) or invert (W/O) emulsion.

According to one particular embodiment, the composition according to the present invention has a low content of additional colorants, different from the color system in accordance with the invention and described above.

According to an even more particular embodiment, the composition according to the present invention is free of additional colorants.

The term "free of colorants" is intended to mean that a composition according to the invention may comprise colorants in a very low content, namely less than 0.1% by weight, or even less than 0.01% by weight, preferably less than 0.001% by weight and even better still less than 0.0005% by weight, relative to the total weight of the composition.

In other words, the presence of this small amount of colorants may possibly color the compositions according to the invention in their bulk, but does not color the deposit that remains after application of the composition to the skin.

According to one variant of the invention, a composition according to the invention comprises at least one aqueous phase, and in particular water, which may form the continuous phase of the composition under consideration.

This aqueous phase may consist totally or partly of water, and preferentially consists essentially of water.

A composition according to the invention may thus comprise a water content of between 1% and 90% by weight of water, preferably greater than 50% by weight of water, or even greater than 60% by weight of water and preferentially greater than 70% by weight of water relative to the total weight of the composition.

According to one preferred embodiment, a composition according to the invention has a water content of between 50% and 90% by weight of water, preferably between 60% and 90% by weight of water and preferentially between 70% and 80% by weight of water relative to the total weight of the composition.

The aqueous phase of a composition according to the invention may also consist of a mixture of water and of a water-miscible organic solvent, for instance lower monoalcohols containing from 2 to 5 carbon atoms such as ethanol or isopropanol, glycols containing from 2 to 8 carbon atoms such as propylene glycol, glycerol, ethylene glycol, 1,3-butylene glycol or dipropylene glycol, $C_3$-$C_4$ ketones and $C_2$-$C_4$ aldehydes, and preferably a glycol containing from 2 to 8 carbon atoms, preferably glycerol.

A composition according to the invention may also contain a fatty phase, preferably a fatty phase dispersed in the continuous aqueous phase presented above, so as to form an emulsion of oil-in-water or water-in-oil type, preferably an oil-in-water emulsion.

An emulsion according to the invention may also be in the form of a multiple emulsion, namely of water-in-oil-in-water or oil-in-water-in-oil type.

The fatty phase of a composition of the invention may in particular comprise at least one fatty substance that is liquid at ambient temperature and/or a fatty substance that is solid at ambient temperature, such as waxes, pasty fatty substances and gums, and mixtures thereof.

For the purposes of the invention, the term "ambient temperature" is intended to mean a temperature equal to 25° C.

The fatty phase of the composition according to the invention may in particular comprise, as liquid fatty substance, at least one volatile or non-volatile oil or a mixture thereof.

For the purposes of the invention, the term "volatile oil" is intended to mean any oil that is capable of evaporating on contact with the skin in less than one hour, at ambient temperature and atmospheric pressure.

The term "non-volatile oil" is intended to mean an oil that remains on the skin at ambient temperature and atmospheric pressure for at least several hours, and that in particular has a vapor pressure of less than 0.01 mmHg (1.33 Pa).

These volatile or non-volatile oils may be hydrocarbon-based oils or silicone oils, or mixtures thereof. The term "hydrocarbon-based oil" is intended to mean an oil mainly containing hydrogen and carbon atoms and optionally oxygen, nitrogen, sulfur or phosphorus atoms.

Volatile hydrocarbon-based oils may be chosen from hydrocarbon-based oils containing from 8 to 16 carbon atoms, and in particular branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar® or Permethyl®, branched $C_8$-$C_{16}$ esters such as isohexyl neopentanoate, and mixtures thereof. Other volatile hydrocarbon-based oils, for instance petroleum distillates, in particular those sold under the name Shell Solt® by the company Shell, may also be used.

Volatile oils that may also be used include volatile silicones, for instance volatile linear or cyclic silicone oils, in particular those with a viscosity 8 centistokes ($8 \times 10^{-6}$ m$^2$/s) and in particular containing from 2 to 7 silicon atoms, these silicones optionally comprising alkyl or alkoxy groups containing from 1 to 10 carbon atoms. Mention may in particular be made, as volatile silicone oils which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and mixtures thereof.

The volatile oil may be present in a composition according to the invention in a content ranging from 0.1% to 98% by weight, in particular from 1% to 65% by weight and in particular from 2% to 50% by weight relative to the total weight of the composition.

The non-volatile oils may be chosen in particular from non-volatile hydrocarbon-based, fluoro and/or silicone oils.

Non-volatile hydrocarbon-based oils that may in particular be mentioned include:

hydrocarbon-based oils of animal origin, hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are in particular wheatgerm oil, sunflower oil, grapeseed oil, sesame seed oil, corn oil, apricot oil, castor oil, shea oil, avocado oil, olive oil, soybean oil, sweet almond oil, palm oil, cottonseed oil, hazelnut oil, macadamia oil, jojoba oil, alfalfa oil, poppy oil, pumpkin oil, sesame seed oil, marrow oil, rapeseed oil, blackcurrant oil, evening primrose oil, millet oil, barley oil, *quinoa* oil, rye oil, safflower oil, candlenut oil, passion flower oil and musk rose oil; shea butter; or alternatively caprylic/capric acid triglycerides such as those sold by the company Stéarineries Dubois or those sold under the names Miglyol® 810, 812 and 818 by the company Dynamit Nobel, synthetic ethers containing from 10 to 40 carbon atoms;

linear or branched hydrocarbons of mineral or synthetic origin, such as petroleum jelly, polydecenes, hydrogenated polyisobutene such as Parleam, and squalane, and mixtures thereof, preferably petroleum jelly, synthetic esters such as oils of formula $R_1COOR_2$ in which $R_1$ represents a linear or branched fatty acid residue containing from 1 to 40 carbon atoms and $R_2$ represents an in particular branched hydrocarbon-based chain containing from 1 to 40 carbon atoms, on condition that $R_1+R_2 \geq 10$, for instance purcellin oil (cetostearyl octanoate), isopropyl myristate, isopropyl palmitate, $C_{12}$-$C_{15}$ alkyl benzoates, hexyl laurate, diisopropyl adipate, isononyl isononanoate, 2-ethylhexyl palmitate, isostearyl isostearate, alkyl or polyalkyl heptanoates, octanoates, decanoates or ricinoleates such as propylene glycol dioctanoate; hydroxylated esters such as isostearyl lactate and diisostearyl malate; polyol esters and pentaerythritol esters, fatty alcohols that are liquid at ambient temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol, and higher fatty acids such as oleic acid, linoleic acid or linolenic acid, and mixtures thereof.

The nonvolatile silicone oils that may be used in the compositions according to the invention may be nonvolatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethi cones, phenyl dimethicones, phenyltrimethylsiloxydiphenylsiloxanes, diphenyl dimethicones, diphenylmethyldiphenyltrisiloxanes and 2-phenylethyl trimethylsiloxysilicates. The non-volatile oils may be present in a composition according to the invention in a content ranging from 0.01% to 90% by weight, in particular from 0.1% to 85% by weight and in particular from 1% to 70% by weight relative to the total weight of the composition.

A composition according to the invention may also contain emulsifying and co-emulsifying surfactants present in particular in a proportion ranging from 0.1% to 30% by weight and in particular ranging from 1% to 15% by weight relative to the total weight of the composition.

These surfactants may be chosen from anionic and nonionic surfactants. Reference may be made to Kirk-Othmer's *Encyclopedia of Chemical Technology*, Volume 22, pp.

333-432, 3rd Edition, 1979, Wiley, for the definition of the properties and functions (emulsifying) of surfactants, in particular pp. 347-377 of this reference, for the anionic and nonionic surfactants.

Preferably, a composition according to the invention is in the form of an emulsion, preferentially an oil-in-water emulsion.

The composition may also be a foundation to be applied to the face or the neck, a concealer product or a skin care cream.

The examples that follow serve to illustrate the invention without, however, being limiting in nature. Unless otherwise indicated, the amounts shown are expressed as percentages by weight.

EXAMPLES

Example 1: Composition with Healthy-Looking Appearance Effect in the Form of an O/W Emulsion Comparative Evaluation of the Cosmeticity/Sensoriality The 15 experts evaluated the following sensory parameters:

The "glidance" of the composition during application (which contrasts with the dragging effect of compositions which catch on application)

The softness of the skin finish once the composition has been applied (which contrasts with the rough, scratchy effect)

The comfort. A comfortable product is defined as a product which does not pull, which does not dry out the skin and which conveys a care effect.

The descriptors are evaluated on a 5-level scale: ++/+/0/−/−−

The experts also evaluated the esthetic appearance (esthetic flash) on the parameter:

The hydratation, evaluation by esthetics expert on the dehydration lines of the face and the eyes.

| Phase | INGREDIENTS | Composition A OUTSIDE THE INVENTION | Composition B ACCORDING TO THE INVENTION |
|---|---|---|---|
| Aqueous phase | WATER | qs 100 | qs 100 |
| | GLYCEROL | 8.5 | 8.5 |
| | PRESERVING AGENT | qs | qs |
| | TETRASODIUM EDTA | 0.10 | 0.10 |
| | ACRYLAMIDE/SODIUM ACRYLOYLDIMETHYLTAURATE COPOLYMER (and) ISOHEXADECANE (and) POLYSORBATE 80[3] | 1.5 | 1.5 |
| Fatty phase | SORBITAN TRISTEARATE | 1 | 1 |
| | PEG-40 STEARATE[4] | 2 | 2 |
| | CETYL ALCOHOL | 3.5 | 3.5 |
| | GLYCERYL STEARATE | 2.8 | 2.8 |
| | ISOSTEARYL NEOPENTANOATE | 5 | 5 |
| | HYDROGENATED POLYISOBUTENE | 5 | 5 |
| | MINERAL OIL | 4 | 4 |
| | DIMETHICONE | 8 | 8 |
| | MICA (and) BISMUTH OXYCHLORIDE (and) IRON OXIDES[1] | | 0.2 |
| | SYNTHETIC FLUORPHLOGOPITE (and) TITANIUM DIOXIDE (and) IRON OXIDES (and) TIN OXIDE[2] | | 0.5 |

[1] Chroma-Lite Red CL 4506 ® from the company BASF Personal Care Ingredients
[2] Syncrystal Ivory sold by the company Eckart
[3] Simulgel 600 sold by the company SEPPIC
[4] Myrj S40-PA-(RB) sold by the company Croda
qs: quantity sufficient. A preserving agent may or may not be added to the composition according to the invention, in the concentration required to prevent contamination of the composition. The nature and the concentration of the preserving agent can vary according to the type of composition and according to the type of means for dispensing the latter.

The compositions were prepared according to techniques known to those skilled in the art.

The only difference between composition A and composition B lies in the presence in composition B of the color system in accordance with the invention.

For each of compositions A and B, the cosmetic properties were evaluated according to the following protocol. The cosmetic properties on application are evaluated, monadically, by a panel of experts trained in the description of care products. The sensory evaluation of the care products by this panel is performed as follows: the products are packaged in opaque jars or pump-action bottles depending on the viscosity of the products. Within the same session, the samples are presented in random order to each panellist.

| | Composition A OUTSIDE THE INVENTION | Composition B ACCORDING TO THE INVENTION |
|---|---|---|
| Glidance during application | ++ + | ++ + |
| Softness of the skin finish | ++ + | ++ + |
| Comfort | ++ + | ++ + |
| Hydratation | ++ + | ++ + |

Conclusion:

Generally, the introduction of the color system according to the invention has no negative impact on the cosmeticity of the base. Compositions A and B are very similar from a sensory point of view. The composition according to the invention glides as well during application as the composition outside the invention, and likewise the skin finish is as soft as with the composition outside the invention. The composition according to the invention is just as comfortable as composition A: the color system does not cause any tautness or drying out. The expert evaluation of the moisturizing effect of these 2 compositions shows, for its part, no difference: composition B according to the invention has good moisturization properties (face and area around the eyes).

Evaluation of the Healthy-Looking Appearance Effect of the Composition According to the Invention Immediate Esthetic Evaluation of the Composition According to the Invention:

Healthy-looking appearance: enhance the complexion (in terms of color) and/or impart light, brightness without a shiny effect.

Natural effect: match between the skin finish of the product and the color of the consumer's skin.

Covering effect: lack of uniformity on application, problem of traces and of non-uniformity after application.

The descriptors are evaluated on a 5-level scale: ++/+/0/−/−−

|  | Evaluation of the healthy-looking appearance | Natural effect | Covering effect |
|---|---|---|---|
| On white complexion (phototype I) | ++ Color of the skin enhanced and brightness imparted | ++ | −− Good uniformity on application |
| On intermediate complexion (phototype III) | ++ Color of the skin enhanced and brightness imparted | ++ | −− Good uniformity on application |
| On matte complexion (phototype IV/V) | ++ brightness, light imparted, without shiny effect | ++ | −− Good uniformity on application |

In summary: the composition according to the invention has the distinctive characteristic:
- of not exhibiting a covering effect (uniformity on application),
- of providing a very-natural-skin effect, whatever the complexion/phototype of the skin to which the composition is applied,
- of not producing a negative impact on the cosmeticity of the composition.

The healthy-looking appearance effect of the application of the composition according to the invention can also be measured by the increase in the chromaticity and in the luminance of the skin after application. Said chromaticity and luminance can for example be given a number in the C.I.E.L. $L^*a^*b^*$ system. The healthy-looking appearance effect according to the invention is reflected by an increase in the chromaticity of the skin in the red, pink and/or red-pink range. The observed brightness imparted is reflected, for its part, by an increase in the luminance of the skin after application of the composition.

Example 2: Composition with Healthy-Looking Appearance Effect in the Form of an O/W Emulsion—Evaluation of the Contents in Color System

| | | COMPOSITIONS | | | | | | |
|---|---|---|---|---|---|---|---|---|
| Phase | INGREDIENTS | A OUTSIDE THE INVENTION | C OUTSIDE THE INVENTION | D | E | F | G | H OUTSIDE THE INVENTION |
| | | | | COMPOSITION according to the invention | | | | |
| Aqueous phase | WATER | qs 100 | qs 100 | qs 100 | qs 100 | qs 100 | qs 100 | qs 100 |
| | GLYCEROL | 8.5 | 8.5 | 8.5 | 8.5 | 8.5 | 8.5 | 8.5 |
| | PRESERVING AGENT | qs | qs | qs | qs | qs | qs | qs |
| | TETRASODIUM EDTA | 0.10 | 0.10 | 0.10 | 0.10 | 0.10 | 0.10 | 0.10 |
| | ACRYLAMIDE/SODIUM ACRYLOYLDIMETHYL TAURATE | 1.5 | 1.5 | 1.5 | 1.5 | 1.5 | 1.5 | 1.5 |

-continued

| Phase | INGREDIENTS | A OUTSIDE THE INVENTION | C OUTSIDE THE INVENTION | D | E | F | G | H OUTSIDE THE INVENTION |
|---|---|---|---|---|---|---|---|---|
| | | | | COMPOSITION according to the invention | | | | |
| Fatty phase | COPOLYMER (and) ISOHEXADECANE (and) POLYSORBATE 80[3] SORBITAN TRISTEARATE | 1 | 1 | 1 | 1 | 1 | 1 | 1 |
| | PEG-40 STEARATE[4] | 2 | 2 | 2 | 2 | 2 | 2 | 2 |
| | CETYL ALCOHOL | 3.5 | 3.5 | 3.5 | 3.5 | 3.5 | 3.5 | 3.5 |
| | GLYCERYL STEARATE | 2.8 | 2.8 | 2.8 | 2.8 | 2.8 | 2.8 | 2.8 |
| | ISOSTEARYL NEOPENTANOATE | 5 | 5 | 5 | 5 | 5 | 5 | 5 |
| | HYDROGENATED POLYISOBUTENE | 5 | 5 | 5 | 5 | 5 | 5 | 5 |
| | MINERAL OIL | 4 | 4 | 4 | 4 | 4 | 4 | 4 |
| | DIMETHICONE | 8 | 8 | 8 | 8 | 8 | 8 | 8 |
| | MICA (and) BISMUTH OXYCHLORIDE (and) IRON OXIDES[1] | | 0.1 | 0.2 | 0.5 | 0.65 | 0.7 | 0.8 |
| | SYNTHETIC FLUORPHLOGOPITE (and) TITANIUM DIOXIDE (and) IRON OXIDES (and) TIN OXEDE[2] | | 0.2 | 0.25 | 0.5 | 0.6 | 0.7 | 0.8 |

[1] Chroma-Lite Red CL 4506® from the company BASF Personal Care Ingredients
[2] Syncrystal Ivory sold by the company Eckart
[3] Simulgel 600 sold by the company SEPPIC
[4] Myrj S40-PA-(RB) sold by the company Croda qs: quantity sufficient. A preserving agent may or may not be added to the composition according to the invention, in the concentration required to prevent contamination of the composition. The nature and the concentration of the preserving agent can vary according to the type of composition and according to the type of means for dispensing the latter.

The compositions were prepared according to techniques known to those skilled in the art.

For each of compositions C to H, the cosmetic properties were evaluated according to the protocol already described in Example 1 above.

The results are collated hereinafter.

Comparative Evaluation of the Cosmeticity/Sensoriality

| | | A OUTSIDE THE INVENTION | C OUTSIDE THE INVENTION | D | E | F | G | H OUTSIDE THE INVENTION |
|---|---|---|---|---|---|---|---|---|
| | | | | COMPOSITION according to the invention | | | | |
| Sensory aspects | Glidance during application | ++ | ++ | ++ | ++ | ++ | + | 0 |
| | Softness of the skin finish | ++ | ++ | ++ | ++ | ++ | ++ | 0 |
| | Comfort | ++ | ++ | ++ | ++ | ++ | + | 0 |
| Immediate esthetic evaluation | Evaluation of the healthy-looking appearance | 0 | 0 | + | ++ | ++ | ++ | ++ |
| | Natural effect | 0 | ++ | ++ | ++ | ++ | + | 0 |
| On intermediate complexion (phototype III) | Covering effect | 0 | −− | −− | −− | −− | − | + |

Composition C does not convey a sufficient healthy-looking appearance effect. The healthy-looking appearance effect is obtained from composition D. Compositions D, E, F and G are according to the invention: they convey a natural, healthy-looking appearance effect without coverage, while guaranteeing a sensoriality identical to that of the composition outside the invention. Composition H conveys a healthy-looking appearance effect, but does not guarantee a good enough sensoriality: less glidance, less soft and less comfortable than composition A outside the invention.

This example very clearly brings to light the appropriate limits for obtaining the desired compromise in terms of sensory effects, healthy-looking appearance effect and natural effect.

Example 3: Composition with Healthy-Looking Appearance Effect in the Form of an O/W Emulsion

| Phase | INGREDIENTS | Composition I OUTSIDE THE INVENTION | Composition II ACCORDING TO THE INVENTION |
|---|---|---|---|
| Aqueous phase | WATER | qs 100 | qs 100 |
| | GLYCEROL | 9 | 9 |
| | PRESERVING AGENT | qs | qs |
| | DISODIUM EDTA | 0.1 | 0.1 |
| | POLYACRYLOYLDIMETHYL AMMONIUM TAURATE[3] | 1 | 1 |
| Aqueous phase | POLYACRYLAMIDE (and) C13-14 ISOPARAFFIN (and) LAURETH-7[4] | 0.9 | 0.9 |
| Fatty phase | CETYL ALCOHOL | 1.5 | 1.5 |
| | PEG-100 STEARATE[5] | 0.20 | 0.20 |
| | ISOHEXADECANE | 3 | 3 |
| | DISODIUM STEAROYL GLUTAMATE | 0.30 | 0.30 |
| | CETEARYL ALCOHOL (and) CETEARYL GLUCOSIDE | 0.60 | 0.60 |
| | STEARIC ACID | 0.6 | 0.6 |
| | BEHENYL ALCOHOL | 1.65 | 1.65 |
| | SQUALANE | 1 | 1 |
| | MINERAL OIL | 1 | 1 |
| | ISOSTEARYL NEOPENTANOATE | 4.5 | 4.5 |
| | DIMETHICONE | 2 | 2 |
| | MICA (and) BISMUTH OXYCHLORIDE (and) IRON OXIDES[1] | | 0.5 |
| | SYNTHETIC FLUORPHLOGOPITE (and) TITANIUM DIOXIDE (and) IRON OXIDES (and) TIN OXEDE[2] | | 0.5 |

[1]Chroma-Lite Red CL 4506 ® from the company BASF Personal Care Ingredients
[2]Syncrystal Ivory sold by the company Eckart
[3]Hostacerin AMPS sold by the company Clariant
[4]Sepigel 305 sold by the company SEPPIC
[5]Myrj S100-PA-(SG) sold by the company Croda
qs: quantity sufficient. A preserving agent may or may not be added to the composition according to the invention, in the concentration required to prevent contamination of the composition. The nature and the concentration of the preserving agent can vary according to the type of composition and according to the type of means for dispensing the latter.

The compositions were prepared according to techniques known to those skilled in the art.

For each of compositions I and II, the cosmetic properties were evaluated according to the protocol already described in Example 1 above.

The results are collated hereinafter.

Comparative Evaluation of the Cosmeticity/Sensoriality

| | Composition I OUTSIDE THE INVENTION | Composition II ACCORDING TO THE INVENTION |
|---|---|---|
| Glidance during application | +++ | +++ |
| Softness of the skin finish | +++ | +++ |
| Comfort | +++ | +++ |
| Hydration | +++ | +++ |

Conclusion:

Generally, the introduction of the color system has no negative impact on the cosmeticity of the base. Compositions I and II are very similar from a sensory point of view. The composition according to the invention glides as well during application as composition I outside the invention, and likewise the skin finish is as soft as with the composition outside the invention. The composition according to the invention is just as comfortable as composition I: the color system does not cause any tautness or drying out. The evaluation by an expert of the moisturizing effect of these 2 compositions shows, for its part, no difference: composition II according to the invention has good moisturization properties (face and area around the eyes).

Evaluation of the Healthy-Looking Appearance Effect of the Composition According to the Invention The evaluation of the healthy-looking appearance effect was carried out according to the protocol set out above in Example 1.

The results are collated in the table below.

| | Evaluation of the healthy-looking appearance | Natural effect | Covering effect |
|---|---|---|---|
| On white complexion (Phototype I) | ++ Color of the skin enhanced + brightness imparted | ++ | -- Good uniformity on application |
| On intermediate complexion (phototype III) | ++ Color of the skin enhanced + brightness imparted | ++ | -- Good uniformity on application |

| | Evaluation of the healthy-looking appearance | Natural effect | Covering effect |
|---|---|---|---|
| On matte complexion (phototype IV/V) | ++ brightness, light imparted, without shiny effect | ++ | -- Good uniformity on application |

In summary: the composition according to the invention has the distinctive characteristic:
- of not exhibiting a covering effect (uniformity on application),
- of providing a very-natural-skin effect, whatever the complexion/phototype of the skin to which the composition is applied,
- of not producing a negative impact on the cosmeticity of the composition.

Example 4 Comparison of a Composition of "BB Cream" Foundation Type and a Composition According to the Invention The objective of the present example is to show that, compared with a "BB cream" composition, a composition according to the present invention retains good sensory properties, that it does not have the drawback of coverage and that the skin retains a natural effect.

| Phase | INGREDIENTS | Composition III ACCORDING TO THE INVENTION | Composition IV OUTSIDE THE INVENTION |
|---|---|---|---|
| Aqueous phase | WATER | qs 100 | qs 100 |
| | GLYCEROL | 8.5 | 8.5 |
| | PRESERVING AGENT | qs | qs |
| | TETRASODIUM EDTA | 0.10 | 0.10 |
| | ACRYLAMIDE/SODIUM ACRYLOYLDIMETHYLTAURATE COPOLYMER (and) ISOHEXADECANE (and) POLYSORBATE 80[3] | 1.5 | 1.5 |
| Fatty phase | SORBITAN TRISTEARATE | 1 | 1 |
| | PEG-40 STEARATE[4] | 2 | 2 |
| | CETYL ALCOHOL | 3.5 | 3.5 |
| | GLYCERYL STEARATE | 2.8 | 2.8 |
| | ISOSTEARYL NEOPENTANOATE | 5 | 5 |
| | HYDROGENATED POLYISOBUTENE | 5 | 5 |
| | MINERAL OIL | 4 | 4 |
| | DIMETHICONE | 8 | 8 |
| | MICA (and) BISMUTH OXYCHLORIDE (and) IRON OXIDES[1] | 0.4 | |
| | SYNTHETIC FLUORPHLOGOPITE (and) TITANIUM DIOXIDE (and) IRON OXIDES (and) TIN OXIDE[2] | 0.5 | |
| | TITANIUM OXIDE (UNTREATED ANATASE) (CI: 77891) | | 4.5 |
| | YELLOW IRON OXIDE (CI: 77492) | | 0.7 |
| | RED IRON OXIDE (CI: 77491) | | 0.3 |
| | BLACK IRON OXIDE (CI: 77499) | | 0.1 |

[1] Chrom a-Lite Red CL 4506 ® from the company BASF Personal Care Ingredients
[2] Syncrystal Ivory sold by the company Eckart
[3] Simulgel 600 sold by the company SEPPIC
[4] Myrj S40-PA-(RB) sold by the company Croda qs: quantity sufficient. A preserving agent may or may not be added to the composition according to the invention, in the concentration required to prevent contamination of the composition. The nature and the concentration of the preserving agent can vary according to the type of composition and according to the type of means for dispensing the latter.

The compositions were prepared according to techniques known to those skilled in the art.

Comparative Evaluation of Cosmeticity/Sensoriality

| | | Composition III ACCORDING TO THE INVENTION | Composition IV OUTSIDE THE INVENTION |
|---|---|---|---|
| Sensory aspects | Glidance during application | ++ | - |
| | Softness of the skin finish | ++ | - |
| | Comfort | ++ | - |
| Immediate esthetic evaluation | Evaluation of the healthy-looking appearance | ++ | ++ |
| On intermediate complexion (phototype III) | Natural effect | ++ | - |
| | Covering effect | -- | ++ |

The composition according to the invention provides a healthy-looking appearance effect, without coverage and with a natural skin finish. On the other hand, the "BB cream" composition provides a skin effect (healthy-looking appearance effect) but with coverage and a skin finish that is not very natural (of foundation type). Furthermore, the "BB cream" composition has degraded sensory properties given the content of pigments which bring about a dragging effect, a lack of comfort and a coarse skin finish. Consequently, the composition according to the invention exhibits good cosmetic properties.

Example 5: Composition with Healthy-Looking Appearance Effect in the Form of an O/W Emulsion

| Phase | INGREDIENTS | Composition A OUTSIDE THE INVENTION | Composition X ACCORDING TO THE INVENTION |
|---|---|---|---|
| Aqueous phase | WATER | qs 100 | qs 100 |
| | GLYCEROL | 8.5 | 8.5 |
| | PRESERVING AGENT | qs | qs |
| | TETRASODIUM EDTA | 0.10 | 0.10 |
| | ACRYLAMIDE/SODIUM ACRYLOYLDIMETHYLTAURATE COPOLYMER (and) ISOHEXADECANE (and) POLYSORBATE 80[3] | 1.5 | 1.5 |
| Fatty phase | SORBITAN TRISTEARATE | 1 | 1 |
| | PEG-40 STEARATE[4] | 2 | 2 |
| | CETYL ALCOHOL | 3.5 | 3.5 |
| | GLYCERYL STEARATE | 2.8 | 2.8 |
| | ISOSTEARYL NEOPENTANOATE | 5 | 5 |
| | HYDROGENATED POLYISOBUTENE | 5 | 5 |
| | MINERAL OIL | 4 | 4 |
| | DIMETHICONE | 8 | 8 |
| | MICA (and) BISMUTH OXYCHLORIDE (and) IRON OXIDES[1] | | 0.22 |
| | SYNTHETIC FLUORPHLOGOPITE (and) TITANIUM DIOXIDE (and) IRON OXIDES (and) TIN OXIDE[2] | | 0.74 |

[1]Chroma-Lite Red CL 4506 ® from the company BASF Personal Care Ingredients
[2]Syncrystal Ivory sold by the company Eckart
[3]Simulgel 600 sold by the company SEPPIC
[4]Myrj S40-PA-(RB) sold by the company Croda qs: quantity sufficient. A preserving agent may or may not be added to the composition according to the invention, in the concentration required to prevent contamination of the composition. The nature and the concentration of the preserving agent can vary according to the type of composition and according to the type of means for dispensing the latter.

The compositions were prepared according to techniques known to those skilled in the art.

The only difference between composition A and composition X lies in the presence in composition X of the color system in accordance with the invention.

For each of compositions A and X, the cosmetic properties were evaluated according to the protocol already described in Example 1 above.

The results are collated hereinafter.

Comparative Evaluation of the Cosmeticity/Sensoriality

| | | Composition A OUTSIDE THE INVENTION | Composition X ACCORDING TO THE INVENTION |
|---|---|---|---|
| Sensory aspects | Glidance during application | ++ | ++ |
| | Softness of the skin finish | ++ | ++ |
| | Comfort | ++ | ++ |
| Immediate esthetic evaluation | Evaluation of the healthy-looking appearance | / | ++ |
| On intermediate complexion (phototype III) | Natural effect | / | + |
| | Covering effect | / | -- |

In summary: the composition according to the invention has the distinctive characteristic:

- of not exhibiting a covering effect (uniformity on application),
- of providing a very-natural-skin effect, whatever the complexion/phototype of the skin to which the composition is applied,
- of not producing a negative impact on the cosmeticity of the composition.

Example 6: Composition with Healthy-Looking Appearance Effect in the Form of an Invert Emulsion

| Phase | INGREDIENTS | Composition L OUTSIDE THE INVENTION | Composition M ACCORDING TO THE INVENTION |
|---|---|---|---|
| Aqueous phase | WATER | qs 100 | qs 100 |
| | GLYCEROL | 9 | 9 |
| | PRESERVING AGENT | qs | qs |
| | SODIUM POLYACRYLATE | 0.45 | 0.45 |
| | DISODIUM EDTA | 0.1 | 0.1 |
| | SODIUM ACRYLATES COPOLYMER (and) CAPRYLIC/CAPRIC TRIGLYCERIDE[3] | 2.00 | 2.00 |
| Fatty phase | DIMETHICONE (and) DIMETHICONE/PEG-10/15 CROSSPOLYMER[4] | 4.5 | 4.5 |
| | DIMETHICONE (and) DIMETHICONE/POLYGLYCERIN-3 CROSSPOLYMER[5] | 4 | 4 |
| | ISOHEXADECANE | 4 | 4 |
| | CYCLOHEXASILOXANE | 2 | 2 |
| | DIMETHICONE | 5 | 5 |
| | PEG-10 DIMETHICONE | 1 | 1 |
| | DISTEARDIMONIUM HECTORITE | 0.65 | 0.65 |
| Denatured alcohol | DENATURED ALCOHOL | 1.5 | 1.5 |
| | MICA (and) BISMUTH OXYCHLORIDE (and) IRON OXIDES[1] | | 0.6 |
| | SYNTHETIC FLUORPHLOGOPITE (and) TITANIUM DIOXIDE (and) IRON OXIDES (and) TIN OXEDE[2] | | 0.45 |

[1]Chroma-Lite Red CL 4506 ® from the company BASF Personal Care Ingredients
[2]Syncrystal Ivory sold by the company Eckart
[3]Luvigel EM sold by the company BASF
[4]KSG-210 sold by the company SHIN ETSU
[5]KSG 710 sold by the company SHIN ETSU
qs: quantity sufficient. A preserving agent may or may not be added to the composition according to the invention, in the concentration required to prevent contamination of the composition. The nature and the concentration of the preserving agent can vary according to the type of composition and according to the type of means for dispensing the latter.

The compositions were prepared according to techniques known to those skilled in the art.

The only difference between composition L and composition M lies in the presence in composition M of the color system in accordance with the invention.

For each of compositions L and M, the cosmetic properties were evaluated according to the protocol already described in Example 1 above.

The results are collated hereinafter.

Comparative Evaluation of Cosmeticity/Sensoriality

| | Composition L OUTSIDE THE INVENTION | Composition M ACCORDING TO THE INVENTION |
|---|---|---|
| Glidance during application | ++ + | ++ + |
| Softness of the skin finish | ++ + | ++ + |
| Comfort | ++ + | ++ + |
| Hydration | ++ + | ++ + |

Conclusion:

Generally, the introduction of the color system has no negative impact on the cosmeticity of the base. Compositions L and M are very similar from a sensory point of view. The composition according to the invention glides as well during application as composition L outside the invention, and likewise the skin finish is as soft as with the composition outside the invention. The composition according to the invention is just as comfortable as composition L: the color system does not cause any tautness or drying out. The evaluation by an expert of the moisturizing effect of these 2 compositions shows, for its part, no difference: composition M according to the invention has good moisturization properties (face and area around the eyes).

Evaluation of the Healthy-Looking Appearance Effect of the Composition According to the Invention

|  | Evaluation of the healthy-looking appearance | Natural effect | Covering effect |
| --- | --- | --- | --- |
| On white complexion (Phototype I) | ++ Color of the skin enhanced + brightness imparted | ++ | -- Good uniformity on application |
| On intermediate complexion (Phototype III) | ++ Color of the skin enhanced + brightness imparted | ++ | -- Good uniformity on application |
| On matte complexion (Phototype IV/V) | ++ brightness, light imparted, without shiny effect | ++ | -- Good uniformity on application |

In summary: the composition according to the invention has the distinctive characteristic:
- of not exhibiting a covering effect (uniformity on application),
- of providing a very-natural-skin effect, whatever the complexion/phototype of the skin to which the composition is applied,
- of not producing a negative impact on the cosmeticity of the composition.

The invention claimed is:

1. A cosmetic composition comprising:
composite particles comprising a substrate containing mica and bismuth oxychloride coated with red iron oxide,
at least one nacre comprising a synthetic fluorphlogopite support coated with at least one titanium dioxide layer, and comprising one or more layers of tin oxide and iron oxide, and
a physiologically acceptable medium;
wherein the composite particles are present in said composition in a content ranging from 0.15% to 0.75% by weight, relative to the total weight of the composition, and
wherein the at least one nacre is present in said composition in a content of between 0.25% and 0.75% by weight, relative to the total weight of the composition.

2. The cosmetic composition according to claim 1, in which the composite particles are present in said composition in a content ranging from 0.2% to 0.5% by weight, relative to the total weight of the composition.

3. The cosmetic composition according to claim 1, in which a single nacre is present.

4. The cosmetic composition according to claim 1, in which the support represents 28% to 90% by weight, relative to the total weight of the at least one nacre.

5. The cosmetic composition according to claim 1, in which the at least one nacre comprises titanium dioxide, in a content ranging from 1% to 55% by weight, relative to the total weight of the at least one nacre.

6. The cosmetic composition according to claim 1, in which the at least one nacre comprises iron oxide in a content ranging from 0.5% to 60% by weight, relative to the total weight of the at least one nacre.

7. The cosmetic composition according to claim 1, in which the at least one nacre comprises iron oxide in a content ranging from 0.5% to 25% by weight, relative to the total weight of the at least one nacre.

8. The cosmetic composition according to claim 1, in which the at least one nacre comprises iron oxide which is chosen from red iron oxide, brown iron oxide, yellow iron oxide, black iron oxide, brown-ferric blue iron oxide or a mixture thereof.

9. The cosmetic composition according to claim 1, in which the at least one nacre comprises tin oxide in a content of less than 15% by weight, relative to the total weight of the at least one nacre.

10. The cosmetic composition according to claim 1, in which the at least one nacre comprises tin oxide in a content of less than 2% by weight, relative to the total weight of the at least one nacre.

11. The cosmetic composition according to claim 1, in which the at least one nacre is in the form of particles having a volume average diameter D ranging from 10 to 40 μm.

12. The cosmetic composition according to claim 1, in which the at least one nacre is present in said composition in a content of between 0.3% and 0.6% by weight, relative to the total weight of the composition.

13. The cosmetic composition according to claim 1, in which the weight ratio between the composite particles comprising a substrate containing mica and bismuth oxychloride coated with red iron oxide, and the at least one nacre, is from 1/5 to 2/1.

14. The cosmetic composition according to claim 1, in which said composition is in the form of a dispersion.

15. A process for making-up the skin, which consists in applying a composition as defined in claim 1, to the surface of the targeted skin.

16. The process according to claim 15, characterized in that said skin is the skin of the face.

17. The process according claim 15, characterized in that the skin is the skin of a person over fifty years old.

18. The cosmetic composition according to claim 1, in which said composition is in the form of an emulsion with a liquid to semi-solid consistency, wherein said emulsion is obtained by dispersion of a fatty phase in an aqueous phase or of an aqueous phase in a fatty phase.

19. The cosmetic composition according to claim 1, in which said composition is in the form of an aqueous gel, a lotion, an emulsified gel or a cream.

20. The cosmetic composition according to claim 1, in which said composition is in the form of a liquid to semi-solid suspension.

21. The cosmetic composition according to claim 1, in which said composition is absent of any additional colorant.

\* \* \* \* \*